US012799438B2

(12) United States Patent
Liu et al.

(10) Patent No.: US 12,799,438 B2
(45) Date of Patent: Nov. 17, 2026

(54) METHOD FOR INDUSTRIALLY PRODUCING MOGROSIDE, FRUCTUS MOMORDICAE SUGAR/WINE AND MANNITOL FROM FRESH FRUCTUS MOMORDICAE

(71) Applicant: Genggui Liu, Guilin (CN)

(72) Inventors: Genggui Liu, Guilin (CN); Runqing Zeng, Guilin (CN); Yizhen Liu, Guilin (CN)

(73) Assignee: Genggui Liu, Guilin (CN)

( * ) Notice: Subject to any disclaimer, the term of this patent is extended or adjusted under 35 U.S.C. 154(b) by 365 days.

(21) Appl. No.: 18/580,387

(22) PCT Filed: Aug. 22, 2023

(86) PCT No.: PCT/CN2023/114159
§ 371 (c)(1),
(2) Date: Jan. 18, 2024

(87) PCT Pub. No.: WO2024/041499
PCT Pub. Date: Feb. 29, 2024

(65) Prior Publication Data
US 2025/0092340 A1 Mar. 20, 2025

(30) Foreign Application Priority Data
Aug. 23, 2022 (CN) ........................ 202211010649.2

(51) Int. Cl.

| | |
|---|---|
| ***C12G 3/024*** | (2019.01) |
| ***A23B 7/152*** | (2006.01) |
| ***A23B 7/154*** | (2006.01) |
| ***A23G 3/38*** | (2006.01) |
| ***C07C 29/74*** | (2006.01) |
| ***C07C 29/76*** | (2006.01) |
| ***C12G 3/026*** | (2019.01) |
| ***C12G 3/04*** | (2019.01) |
| ***C12H 1/04*** | (2006.01) |
| ***C12H 1/07*** | (2006.01) |

(52) U.S. Cl.
CPC .............. *C12G 3/024* (2019.02); *A23B 7/152* (2013.01); *A23B 7/154* (2013.01); *A23G 3/38* (2013.01); *C12G 3/026* (2019.02); *C12G 3/04* (2013.01); *C12H 1/04* (2013.01); *C12H 1/063* (2013.01); *A23V 2002/00* (2013.01); *C07C 29/74* (2013.01); *C07C 29/76* (2013.01)

(58) Field of Classification Search
None
See application file for complete search history.

(56) References Cited

U.S. PATENT DOCUMENTS

2017/0150745 A1* 6/2017 Zhang .................... A23L 27/12
2021/0177022 A1* 6/2021 Long ........................ A23B 2/90

FOREIGN PATENT DOCUMENTS

| | | | |
|---|---|---|---|
| CN | 204889204 | U | 12/2015 |
| CN | 109320400 | A | 2/2019 |
| CN | 113142538 | A | 7/2021 |
| CN | 114276885 | A | 4/2022 |
| CN | 114287561 | A | 4/2022 |
| CN | 114292307 | A | 4/2022 |
| CN | 115109112 | A | 9/2022 |
| CN | 115226762 | A | 10/2022 |
| CN | 115403647 | A | 11/2022 |

OTHER PUBLICATIONS

English translation of CN109320400A (cited by IDS).*

* cited by examiner

*Primary Examiner* — Emily M Le
*Assistant Examiner* — Amanda S. Hawkins
(74) *Attorney, Agent, or Firm* — NKL Law; Allen Xue

(57) ABSTRACT

A method for industrially producing mogroside, *fructus momordicae* sugar/wine and mannitol from fresh *fructus momordicae*. The method includes the following steps: freshness-preserving and post-ripening: intervally spraying a mixed aqueous solution of ε-polylysine hydrochloride and calcium propionate, while intervally activating an ozone cycle; and spraying an aqueous solution of ethephon during post-ripening; preparation of mogroside: obtaining mogroside by subjecting the fresh-preserved and post-ripened *fructus momordicae* to water extraction, microfiltration, gradient processing with combined resins, concentration and spray-drying; preparation of *fructus momordicae* sugar: obtaining *fructus momordicae* sugar by compounding the mogroside and a non-sugar sweet substance; preparation of *fructus momordicae* wine: obtaining *fructus momordicae* wine by subjecting a macroporous adsorption resin effluent to fermentation and distillation to obtain a distillate, and then formulating same with the mogroside; and preparation of mannitol: obtaining mannitol by subjecting a distillation bottom liquor during the distillation of the *fructus momordicae* wine to microfiltration, nanofiltration, concentration and crystallization.

9 Claims, No Drawings

METHOD FOR INDUSTRIALLY PRODUCING MOGROSIDE, FRUCTUS MOMORDICAE SUGAR/WINE AND MANNITOL FROM FRESH FRUCTUS MOMORDICAE

TECHNICAL FIELD

The present disclosure belongs to the fields of plant extraction and separation technology and food, and in particular to a method for industrially producing mogroside, *fructus momordicae* sugar/wine and mannitol from fresh *fructus momordicae.*

BACKGROUND

Siraitia grosvenorii (Swingle) C. Jeffrey, also known as *fructus momordicae*, is the fruits of perennial vine of *Cucurbitaceae*. It is known as the "monk fruit" and is mainly produced in places such as Longjiang Township and Baishou Town, Yongfu County, Longsheng Various Nationalities Autonomous County, and Lingui District, etc., of Guilin City, Guangxi Zhuang Autonomous Region. *Fructus momordicae* is one of the first batch of medicinal and edible varieties approved by the country, and has main efficacies of moistening the lungs for arresting cough, and promoting fluid and dissipating phlegm.

*Fructus momordicae* and seedless *fructus momordicae* contain rich flavor and nutritional ingredients, as well as non-sugar sweet ingredients of triterpenoid saponins: cucurbitane-type triterpenoid saponins, mainly mogroside V, IV, 11-O-mogroside V, and siamenoside, etc., with the fresh fruit content of 0.3-0.5%, where the mogroside V is a main sweet ingredient, non-toxic, low-calorie, high-sweetness, and good in thermal stability, and the content of which is the main standard for evaluating the quality of fresh *fructus momordicae*; reducing sugars such as glucose, fructose, and sucrose, etc., with the fresh fruit content of 9-14%; amino compounds such as proteins and amino acids, etc., with the dry fruit content of 7.1%-7.8%; and fatty acids, flavonoid compounds, vitamin C, as well as 26 inorganic and trace elements such as manganese, iron, nickel, selenium, tin, iodine, and molybdenum, etc.

I. Mogroside

Mogroside is a non-sugar sweet component contained in the fruits of *fructus momordicae*, which is mainly triterpenoid saponin with mogrol as aglucon, represented by mogroside V and IV. Among them, the sweetness of the mogroside V is 256-344 folds of that of sucrose, and the sweetness of the mogroside IV is 126 folds of that of sucrose.

Sweet *fructus momordicae* triterpenoid saponins mainly include 11-O-mogroside V. neomogroside, mogroside V, mogroside IV, isomogroside V, siamenoside I, mogroside VI, mogroside IVe, and mogroside Na, etc.

II. *Fructus momordicae* Sugar

*Fructus momordicae* sugar is a kind of natural, zero-calorie or low-calorie ecological green food made by compounding mogroside and a non-sugar sweet substance, such as erythritol, arabinose, allulose, and mannitol, etc. It is a kind of sugar suitable for all populations, especially those with diabetes, hypertension, obesity and not suitable for sugar consumption, can be used as a table sweetener and is an ideal substitute for sucrose.

III. Freshness-Preserving and Post-Ripening of *Fructus Momordicae*

The harvested fruits are still a living organism that undergoes complex life activities such as dormancy, water evaporation, and respiratory action, etc., while maintaining metabolism that consumes $CO_2$ and expels $CO_2$ and $C_2H_4$. The external factors that affect the metabolic activity and storage effect of fruits mainly include temperature, gas composition, and humidity.

The temperature affects the physical, biochemical, and mutagenic reactions during fruit storage, and is an important factor determining the quality of fruit storage. Low temperature can inhibit respiration and other metabolic processes of fruits, reduce the kinetic energy of water molecules, and reduce the evaporation rate of liquid water, thereby delaying aging and maintaining the freshness and fullness of fruits. The metabolism of plant cells mainly involves oxidation and reduction reactions, where the utilization rate of oxygen determines the rate of metabolism, thereby affecting the quality of fruit storage. As for storing fruits, there is an antagonistic and synergistic effect between appropriate temperature, carbon dioxide, and oxygen, and their interaction is much stronger than the individual effect of a certain factor. The loss of water in the harvested fruits can cause changes in structure, texture, and surface, and therefore reducing water loss plays a crucial role in maintaining the freshness and quality of the fruits. The relative humidity represents the degree of dryness and humidity in the ambient air, is an important factor affecting the quality of fruit storage, and is influenced by temperature and air velocity. The control of the humidity during storage must consider both its impact on the storage quality and its impact on microbial activity.

IV Prior Art

There are many studies on *fructus momordicae* in China, including studies on germplasm resources, seedlings, planting, management and protection, and chemical components of *fructus momordicae*, extraction and separation of main bioactive ingredients such as triterpenoid saponins of mogroside, etc., preparation of *fructus momordicae* concentrated juice, pharmacology, toxicology and terminal application of *fructus momordicae* and mogroside, etc.; there are also some studies on the comprehensive utilization of *fructus momordicae*, and wastes generated during the production process are recycled to produce by-products. However, there are few studies on freshness-preservation, storage, saccharification and post-ripening of *fructus momordicae*, and few studies on the industrial production technology system for the extraction, separation, and deep processing of bioactive ingredients of *fructus momordicae.*

(I) Freshness Preservation, Storage, Saccharification and Post-Ripening of *Fructus Momordicae.*

At present, the common practice is to harvest, sell and process the *fructus momordicae* when it is ripe, and the mode of storage mainly includes outdoor shed storage or indoor stacking, and sold in batches to plant extract enterprises within a short time or baked to prepare dried *fructus momordicae*. Due to the large purchase volume, the main production and processing enterprises of fresh *fructus*

*momordicae* in China adopts direct extraction and processing combined with conventional cold storage for 2-3 months before processing. The storage mode mentioned above, i.e., conventional cold storage at room temperature or for a longer period of time, is at the expense of a bad fruit rate of ≥2%. Although the storage at room temperature is of a relatively short period of time, usually 12-25 days, the conditions are difficult to control, external factors have a significant impact, and the bad fruit rate is high. Although the conventional cold storage has maintained low temperatures and controlled relative humidity, it still has a relatively high bad fruit rate due to prolonged storage time. Besides, during the storage, due to the control problem, dehydration of fresh *fructus momordicae* and other factors affecting the internal quality, the stored fresh *fructus momordicae* is difficult for saccharification and post-ripening, resulting in poor taste and mouthfeel of the processed finished products, i.e., mogroside. In addition, the cold storage time is less than or equal to 3 months, which is not conducive to the storage of a large amount of fresh *fructus momordicae* for a long time in abundant years, and is also not conducive to the macro-regulation of the total amount of plenteous fresh *fructus momordicae*. For a large-scale *fructus momordicae* production and processing enterprise that produces and processes 3,500 tons of fresh *fructus momordicae* per month, if it purchases 30,000 tons of fresh *fructus momordicae* per year and overall considers the influence factors such as corollary equipment of extraction, separation and processing, as well as production continuity, etc., and will not be able to complete the production and processing of fresh *fructus momordicae* in time, resulting in a large amount of bad fruits, and directly causing major economic losses. If fresh *fructus momordicae* is simply processed into an extract concentrate, as the fresh fruits have not yet been saccharified and post-ripened, it will directly lead to poor taste and mouthfeel of the finished product of the *fructus momordicae* extract, thereby seriously affecting the sales of the product. Whether the fresh *fructus momordicae* can be kept fresh will cause large fluctuations in the market price of fresh *fructus momordicae*, which will affect the interests of farmer households and enterprises.

Therefore, it is a bottleneck in the industrialization process of *fructus momordicae* to keep freshness of and store the fresh *fructus momordicae* after harvest for a long time, allow it to normally saccharify and post-ripen, ensure the bulk supply of fresh *fructus momordicae*, carry out market regulation, and maintain the good quality of the processed finished products such as mogroside, concentrated *fructus momordicae* juice, and *fructus momordicae* sugar, etc. Currently, it has not been reported that the long-term freshness preservation and storage of fresh *fructus momordicae* can be achieved by a mixed chemical agent of ε-polylysine hydrochloride and calcium propionate in coordination with ozone conditioning, and synergy with low temperature and high humidity; and by regulating the temperature and relative humidity, concentrations of oxygen and carbon dioxide, recovering and improving the metabolism of freshness-preserved *fructus momordicae*, and producing endogenous ethylene assisted by exogenous ethylene, and inducing the freshness-preserved *fructus momordicae* to produce endogenous ethylene to work together for the ripening so as to achieve the saccharification and post-ripening of fresh preserved *fructus momordicae*.

The technical solutions in the prior art relating to the processing of fresh *fructus momordicae* after harvesting, including extending the storage period and freshness preservation, and promoting saccharification and post-ripening, do not involve in long-term freshness preservation and storage of fresh *fructus momordicae* through the synergistic effect of chemical agents, gas, temperature and relative temperature, which belongs to short-term storage, and also do not involve in forced ripening under the dual influence of temperature and humidity by adding exogenous ethylene.

(II) Extraction and Separation of Bioactive Ingredients from *Fructus Momordicae*

At present, the common practice is to extract a single mogroside from *fructus momordicae* or simultaneously prepare a variety of main products of *fructus momordicae* extracts such as *fructus momordicae* saponin components, concentrated *fructus momordicae* juice, etc., or prepare by-products such as *fructus momordicae* seed oil, amino acid, and dietary fiber from production waste liquid and residue. It is rarely reported that mogroside, concentrated *fructus momordicae* juice and terminal product *fructus momordicae* sugar are simultaneously prepared, and even the by-products such as *fructus momordicae* wine and mannitol are continuously prepared on the same production line. At present, most of the technologies disclosed have certain problems, which can be summarized as follows: (1) Falsely labeled content of mogroside. It is claimed that the purity of mogroside V is more than 90% only through refining and decoloring technologies such as macroporous adsorption resin, ion exchange resin and membrane separation, etc. In fact, it can be known by those skilled in the art that it is impossible to prepare more than 65% of mogroside V by such technologies. At present, the content of mogroside V in the mainstream *fructus momordicae* extracts in the market is only about 50%, and there are very few varieties with the content of 60%. At present, there are only an extremely small number of varieties with higher content available as reagents, and they have not yet been industrially produced. (2) Non-industrial applicability. Laboratory technologies such as preparative liquid-phase separation of mogroside, silica gel chromatography, high-speed countercurrent chromatography separation technology, etc., are complicated in operation and expensive in equipment.

In conclusion, the preparation of mogroside in the prior art is of a single technical purpose and rarely involves the comprehensive utilization of *fructus momordicae* and the simultaneous preparation of a variety of products. Although some involve the use of macroporous adsorption resin combined with ion exchange resin, they violate technical principles and do not involve the gradient processing of hot water-alkali combined with resin to solve the problems of chromatographic column blockage, resin service life, and efficient decolorization during the production. Therefore, with the upgrading and improvement of the technology, it is necessary to establish a relatively perfect industrial production technology system for the extraction, separation, and deep processing of *fructus momordicae*.

SUMMARY

The technical problem to be solved by the invention is to overcome the above shortcomings, and to provide a method for industrially producing mogroside, *fructus momordicae* sugar/wine and mannitol from fresh *fructus momordicae* with fresh and mature *fructus momordicae* as raw materials.

(1) A method for freshness preservation and storage and saccharification and post-ripening of *fructus momordicae* is provided so as to provide high-quality raw materials for *fructus momordicae* industry all the year round, regulate the market of fresh *fructus momordicae*, and solve the problems of storage time, quality, and saccharification and post-ripening after cold storage of fresh *fructus momordicae;*

(2) a simple and practical technology for industrial production of high-quality mogroside changes the complicated and tedious procedures of the prior art, reduces the production processes and steps, improves the recovery rate, refining and decolorization effect of mogroside, product quality and sweetness performance, and solves the problem that chromatographic column blockage during the production affects the service life of resin and reduces the production efficiency; and (3) a relatively perfect production technology system is established for the extraction, separation and deep processing of *fructus momordicae*: the *fructus momordicae* extract of mogroside is mainly prepared and then the terminal product of *fructus momordicae* sugar is prepared by compounding the obtained high-quality mogroside with non-sugar sweet substances simultaneously; production wastes are comprehensively utilized, the wastes are recycled, glucose, sucrose, etc., are subjected to liquid fermentation into a special agricultural and sideline product, i.e., *fructus momordicae* wine in Guilin, Guangxi, and finally, and mannitol is extracted from the bottom liquor after brewing, such that a perfect continuous industrial production technology system for continuous production of four products in the production line is achieved.

The technical solution adopted by the present disclosure to solve the technical problem is as follows: a method for industrially producing mogroside, *fructus momordicae* sugar/wine and mannitol from fresh *fructus momordicae* including the following steps:

S1, freshness-preserving and post-ripening:

(S1-1) fruit sorting and storing: sorting out and removing the old and green fruits and poor-quality fruits from the harvested fresh *fructus momordicae*, and storing the sorted *fructus momordicae* in a warehouse;

(S1-2) freshness-preserving: standing the *fructus momordicae* in the warehouse for 60-240 days and intervally spraying a mixed aqueous solution of ε-polylysine hydrochloride and calcium propionate, while intervally activating the ozone cycle, with a storage condition for freshness-preserving being a temperature of 2-6° C., and a daily relative humidity of 80-90% but 55-65% maintained within 12 hours after each spraying of a chemical agent; and (S1-3) saccharifying and post-ripening: raising a temperature to 22-26° C. at a heating rate of 0.15-0.35° C./h in the warehouse, maintaining the relative humidity of 80-90% during the heating process, and a relative humidity of 70-80% when reaching the target temperature, changing air every 22-26 hours to maintain normal oxygen concentration, absorbing carbon dioxide to adjust the concentration of the carbon dioxide with an alkaline solution, spraying an aqueous solution of ethephon evenly every 4-6 days, and keeping a post-ripening process for 15-30 days;

S2, preparation of mogroside:

(S2-1) water extracting: crushing the saccharified and post-ripened fresh *fructus momordicae* and extracting same with water to obtain an extract;

(S2-2) subjecting the extract to ceramic membrane microfiltration;

(S2-3) gradient processing with combined resins: subjecting a ceramic membrane clear solution to adsorption and desorption of the following resins sequentially: a first macroporous adsorption resin column, an anion exchange resin, and a second macroporous adsorption resin; and then performing desorption to obtain the combined resin refined solution;

(S2-4) concentrating the combined resin refined solution to a concentration of 17-25 Baume degree to obtain a concentrated solution; and (S2-5) spray-drying the concentrated solution to obtain mogroside;

S3. preparation of *fructus momordicae* sugar:

(S3-1) taking an appropriate amount of the mogroside from step (S2) and dissolving same by adding purified water as an adhesive; and (S3-2) charging any one or a composition at any ratio of four non-sugar sweet substances of erythritol, arabinose, allulose, and mannitol into a boiling granulator step by step, spraying the adhesive evenly for boiling granulation, and drying same to obtain the *fructus momordicae* sugar;

S4. preparation of *fructus momordicae* wine:

(S4-1) liquid fermentation of first macroporous adsorption resin effluent: collecting a first macroporous adsorption resin feed effluent in step (S2-3), combining same with a water-washing solution concentrating same to 5-25 Brix, adding a complex enzyme preparation, and fermenting same until a strong wine aroma appears to obtain a fermentation liquor;

(S4-2) distilling the fermentation liquor, collecting a distillation bottom liquor and a distillate separately; and (S4-3) adding the mogroside obtained in step (S2) to the distillate to obtain the *fructus momordicae* wine; and S5. preparation of mannitol:

(S5-1) taking the distillation bottom liquor from step S4, microfiltrating same through a complete set of ceramic membrane equipment, and collecting a filtrate to obtain a ceramic membrane clear solution;

(S5-2) subjecting the ceramic membrane clear solution to nanofiltration for decolorization to obtain a discolored solution; and (S5-3) concentrating the discolored solution and adding ethanol while hot, and cooling same for crystallization to obtain mannitol.

Preferably, in the fruit sorting and storing in step (S1-1), the fruit sorting is to sort out and remove the old and green fruits and poor-quality fruits of *fructus momordicae* that cannot grow and be mature naturally, and only the fresh and mature *fructus momordicae* and seedless *fructus momordicae* harvested in season, which are intact, undamaged and free of mildew and rot, can be put into the warehouse. The old and green fruits and poor-quality fruits cannot be mature under natural conditions due to weather, temperature and other reasons. They are also difficult to preserve and post-ripen according to the method of the present application, which will affect the quality of *fructus momordicae*, and they should be sorted out and removed. The stacking height of the stored fresh *fructus momordicae* is to stack the *fructus momordicae* for 3 to S layers. Too low stacking will cause waste of storage space and is not conducive to the accumulation of volatile substances and mutual promotion of ripening of fresh *fructus momordicae* in the basket during the ripening; and too high stacking will easily exceed the bearing range of the standard basket of *fructus momordicae*, and the fresh *fructus momordicae* will be easily crushed to increase the rate of bad fruits.

Preferably, in the freshness-preserving of step (51-2), the chemical agent is the mixed aqueous solution of ε-polylysine hydrochloride and calcium propionate, where the concentration of the ε-polylysine hydrochloride is 0.1-0.3%, and the concentration of the calcium propionate is 1.0-2.0%, and the chemical agent is sprayed evenly once every 25-30 days. The concentration of the sprayed chemical agent should not be too high or too low. If the concentration is too low, the spray volume needs to be high, which will cause water accumulation on the fresh fruits (the amount of water carried on the surface of fresh *fructus momordicae* is limited). When the relative humidity in the air is too high, water is not easy to be volatilized. If the concentration is too high, the spray volume needs to be small, which cannot moisten the fresh *fructus momordicae* sufficiently. The spraying amount of ε-polylysine hydrochloride and calcium propionate is sufficient to moisten the surface of *fructus momordicae*. In a specific embodiment of the present disclosure, 50-100 mL of a mixed aqueous solution of ε-polylysine hydrochloride and calcium propionate is sprayed per kg of *fructus momordicae*, preferably 60-80 mL.

The ε-polylysine hydrochloride has a broad-spectrum anti-microorganism effect, and the calcium propionate has anti-fungal and moisture-absorbing effects. The combination of the two has a significant anti-bacterial and anti-fungal effect, and a small amount of the calcium propionate has a moisture-absorbing effect, which can maintain water on the surface of the fresh *fructus momordicae*. Ozone has an anti-microorganism effect, eliminates and inhibits ethylene produced by fresh *fructus momordicae* through oxidation, reduces the metabolism, induces the contraction of epidermal stomata of *fructus momordicae* and reduces water loss. However, the ozone will gradually be consumed and lost during use, and thus should be supplemented periodically. Ozone conditioning, combined with the mixed chemical agent of the ε-polylysine hydrochloride and calcium propionate, can significantly enhance the anti-microorganism, sterilizing, and antifungal effects, thus keeping *fructus momordicae* fresh for a long time.

The ozone cycle is activated for 40-60 minutes at an amount of ozone of 5-15 ppm every 14-16 days or after a warehouse door is opened and closed.

Ozone has an anti-microorganism effect, eliminates and inhibits ethylene produced by fresh *fructus momordicae* through oxidation, reduces the metabolism, induces the contraction of epidermal stomata of *fructus momordicae* and reduces water loss. However, the ozone will gradually be consumed and lost during use, and thus should be supplemented periodically. Ozone conditioning, combined with the mixed chemical agent of the ε-polylysine hydrochloride and calcium propionate, can significantly enhance the anti-microorganism, sterilizing, and antifungal effects, thus keeping *fructus momordicae* fresh for a long time.

In the freshness-preserving of step (S1-2), the storage condition is a temperature of 2-6° C. and a daily relative humidity of 80-90% but 55-65% maintained within 12 hours after each spraying of the chemical agent. A lower temperature can significantly improve the freshness-preserving effect of *fructus momordicae* without causing frostbite; and a higher relative humidity can reduce the water loss of *fructus momordicae*, achieves synergetic moisturizing with the chemical agent and ozone, and has a significant effect. After each spraying of the chemical agent, to prevent excessive moisture on the surface of the fresh *fructus momordicae* and avoid deterioration, the relative humidity needs to be controlled in a timely manner to promote water evaporation on the surface. The freshness-preserving period is 60-240 days. For large enterprises that process *fructus momordicae*, the freshness-preserving period matches with the purchase and production devices of fresh *fructus momordicae*. It is of no significance if the fresh *fructus momordicae* is placed for a long time, which will not only increase the cost, but also increase the rate of bad fruits due to the hot weather, causing direct economic losses.

Preferably, in the saccharifying and post-ripening of step (S1-3), the temperature is raised by 1° C. every 3-6 hours from 2-6° C. during the freshness-preserving storage period to 20-26° C. Slow temperature-raising can facilitate fresh *fructus momordicae* to return to a normal state from the low-temperature dormancy, and improves the effect of saccharifying and post-ripening. During the temperature-raising process, the relative humidity is maintained at 80-90%, and when the temperature reaches 20-26° C., the relative humidity is adjusted to 70-80%. Maintaining the original relative humidity during the temperature-raising process can allow the fresh *fructus momordicae* to gradually adapt to the environment and improve its adaptability during the recovery process. When the temperature of saccharifying and post-ripening is reached, lowering the relative humidity can allow *fructus momordicae* to slowly lose a part of water during the post-ripening process, and work together with microorganisms and enzymes to improve the effect of saccharifying and post-ripening.

In the saccharifying and post-ripening of step (S1-3), air is changed every 22-26 hours to maintain normal oxygen concentration; and the alkaline solution is a mixed solution of NaOH and $Ca(OH)_2$, where the concentration of NaOH is 0.2-1.0 wt %, and the $Ca(OH)_2$ is saturated lime water. During the saccharifying and post-ripening process of fresh *fructus momordicae*, the oxygen concentration in the warehouse drops to about 10% at about 22-24 hours, and air needs to be changed to reach the oxygen concentration of about 21% to facilitate the post-ripening of fresh *fructus momordicae*. The aqueous solution of NaOH and $Ca(OH)_2$ can continuously absorb $CO_2$ produced by the respiration of fresh *fructus momordicae*, which reduces the respiratory damage caused by $CO_2$ and significantly reduces the rate of bad fruits.

Preferably, in the saccharifying and post-ripening of step (S1-3), the ripening is achieved by releasing exogenous ethylene using an aqueous solution of ethephon; the concentration of ethephon is 400-800 ppm, and 40-80 mL aqueous solution of ethephon is sprayed per kg *fructus momordicae* evenly once every 4-6 days. After fresh *fructus momordicae* recovers from dormancy, it will produce a certain amount of endogenous ethylene; the aqueous solution of ethephon will not only release ethylene, but also induce fresh *fructus momordicae* to produce endogenous ethylene. By maintaining a certain concentration of the exogenous ethylene and through the combined action of the endogenous and exogenous ethylene, the post-ripening of freshness-preserved *fructus momordicae* fruits can be significantly prompted and the rate of bad fruits is reduced under the conditions of appropriate temperature, relative humidity, oxygen and low carbon dioxide concentration.

Preferably, the saccharifying and ripening time in step (S1-3) is 15-30 days.

Preferably, in step (S2-1), the extraction method is continuous countercurrent extraction or extraction via an extraction tank; and the extraction temperature is 65-99° C. and the extraction solvent is water. In a specific embodiment, the continuous countercurrent extraction is performed for 2-3 hours with the water addition amount of 1.2-3.0 folds (water volume/fresh *fructus momordicae*, V/W); a two-section extraction tank is used, after extraction in each section, squeezing and filtration are performed, and the continuously flowing extracts are combined to obtain a counter-current extract. In another specific embodiment, the extraction is performed via an extraction tank for 1.5-2.5, 1.0-2.0, and 0.5-1.5 hours for a total of 3 times with the water addition amount of 2-4 folds each time (water volume/fresh *fructus momordicae*, V/W). The stirring method is as follows: starting mechanical mixing or compressed air backflushing. After each extraction, filtration is performed, and the first and second extraction residues enter the next extraction, and the first and second extracts are combined to obtain the extract from the extraction tank.

In step (S2-2), the ceramic membrane microfiltration is performed twice to four times, and the temperature is reduced from 45-60° C. to 15-30° C. during the ceramic membrane microfiltration, preferably, the ceramic membrane microfiltration is performed twice, specifically involving cooling the extract to 45-60° C., centrifuging same, and then subjecting same to microfiltration via a first complete set of ceramic membrane equipment to collect a filtrate, further cooling the filtrate to 15-30° C., and then subjecting same to microfiltration via a second complete set of ceramic membrane equipment to collect a filtrate, to obtain the ceramic membrane clear solution.

The *fructus momordicae* extract contains pectin, proteins and other viscous substances, which can easily block the ceramic membrane. At a higher temperature of 45-60° C., the ceramic membrane is not easily blocked and has a large flux, which can achieve microfiltration clarification quickly. If the ceramic membrane clear solution under the condition is fed into a macroporous adsorption resin column, the resin is more likely to harden, causing blockage of the chromatography column. When the ceramic membrane clear solution above 45° C. is further cooled to below 15-30° C., the flux of the ceramic membrane does not decrease significantly. However, the ceramic membrane clear solution under the condition does not cause resin hardening, and the chromatography column will not be blocked. But if the extract is directly cooled to below 30° C. and then clarified through the ceramic membrane microfiltration, the ceramic membrane will be directly blocked and the flux will be extremely small. Therefore, after repeated experiments and demonstrations, the inventor determines that more than twice ceramic membrane microfiltration clarification at high and low temperatures are used as pretreatment before feeding into the chromatography system, and the temperature is gradually reduced from 45-60° C. to 15-30° C., which not only maintains a large ceramic membrane flux and obtains a clear and transparent solution, but also solves the problems of hardening of the macroporous adsorption resin and the blockage of the chromatography column in the industrial production of *fructus momordicae.*

In step (S2-3), the gradient processing with combined resins is specifically as follows: 1) feeding the ceramic membrane clear solution into the first macroporous adsorption resin column, after the feeding, adding 1.5-3.0 BV of hot purified water at a temperature of 50-80° C., and collecting the feed effluent and 1.0-2.5 BV of purified water-washing solution to obtain an effluent; then adding an aqueous solution of NaOH at a temperature of 50-60° C., a concentration of 0.5-0.9 wt %, and a volume of 0.6-1.0 BV for resin column processing at a flow rate of 2-3 BV/h, then adding room-temperature purified water until the pH of the resin column effluent is 6.8-7.5, then desorbing with hydrous ethanol, collecting the desorbed solution, and concentrating and recovering ethanol, to obtain the adsorption resin processed solution; 2) adjusting the sugar degree of the adsorption resin-processed solution to 4-8 Brix, feeding same into a basic anion exchange resin column, and after the feeding, feeding 3-5 BV purified water to rinse the resin column, and collecting the feed effluent and water-washing solution in sequence; and 3) feeding the anion exchange resin column feed effluent and water-washing solution into the macroporous adsorption resin column in sequence, after the feeding, adding 1.5-3.0 BV of room-temperature purified water, then adding 0.6-1.0 BV of an aqueous solution of citric acid with a concentration of 0.3-0.6% for resin column processing, continuously adding purified water until the pH of the resin column effluent is 5.5-7.0, then desorbing with hydrous ethanol and collecting the desorbed solution to obtain the combined resin refined solution. Further, the concentration of ethanol is 50-70% in the hydrous ethanol.

Theoretically, during the purification process of resin column adsorption and desorption, mogroside is partially destroyed in hot alkali, and the content and the recovery rate will be reduced. Therefore, generally the hot alkaline condition should be avoided when purifying mogroside. The inventor unexpectedly found that, if the hot alkali condition is appropriate, the treatment is in time, the time and volume of the hot alkali are controlled, and the purified water is used for treatment in time, the obtained mogroside finished product will be lighter in color, ultimately, the mogroside V content in the mogroside can be increased by 5 wt % to 8 wt %, and the yield of mogroside V is increased. This is an unexpected discovery made by the inventor during an experimental error. The possible reason is that, when the macroporous adsorption resin column is treated with hot alkali, part of the pigments, proteins and other viscous substances, and other impurities can be fully washed out from the resin column, thus increasing the content of mogroside V; another possible reason is that, the competitive adsorption of mogroside by impurities is reduced, such that the adsorption and desorption properties of the mogroside are better, thus improving the yield. The inventor found that careful use of hot alkali can omit the tedious process steps of mogroside purification and improve the purity and yield of the mogroside.

The method of the present disclosure not only reduces the amount of the anion exchange resin used for subsequent decolorization, but also significantly improves the decolorization effect; the taste is very good, and the sweetness is pure. In addition, it solves the problems of blockage of chromatography column and resin hardening. When this batch of products are decolorized and refined with the anion exchange resin, it is directly fed into the second macroporous adsorption resin under the alkaline condition, and treated to neutral in time before desorption. No pesticide residues are detected in the final product of mogroside V50.

The effluent (mogroside in this part) of the alkaline anionic resin is alkaline with a pH of about 10. After the effluent is fed into the second macroporous adsorption resin column, it is decolorized and foreign unknown substances and other ingredients that have an impact on the taste are removed; however, it is not easy to wash the resin column to neutral under the alkaline condition, which not only wastes purified water, but also does not play a special role in the later period. Therefore, a dilute aqueous solution of citric acid is fed into the column to neutralize the alkalinity; i.e., when the alkalinity reaches a certain level, the decolorization and refining effects have been achieved. At this time, the resin column is easily washed to neutral with purified water when it is neutralized to acidic or neutral.

In summary, water is saved and production efficiency is improved.

Preferably, in gradient processing with combined resins in the step (S2-3), the first adsorption resin is a macroporous adsorption resin, including non-polar D101, LX-100B, LX-T28 and the like, and low-polar AB-8, and is used at an amount of 400-550 kg per 1,000 kg of fresh *fructus momordicae*; and a processing method includes after feeding, adding 1.5-3.0 BV of hot purified water at a temperature of 50-80° C., then adding an aqueous solution of NaOH at a temperature of 50-80° C., a concentration of 0.5-1.2% and a volume of 0.6-1.0 BV for resin column processing at a flow rate of 2-3 BV/h, and then adding room-temperature purified water until the pH of the resin column effluent is 6.8-7.5.

Treating the macroporous adsorption resin with hot purified water is conducive to washing out a small amount of viscous substances remaining after clarification through ceramic membrane microfiltration from the resin column. On the basis of the clarification through the ceramic membrane microfiltration, the resin hardening can be further reduced to avoid blockage of a chromatography column. The low-concentration and small-volume hot alkali solution quickly passes through the macroporous adsorption resin column. The loss rate of the mogroside caused by a single factor is ≤3%. The color (obtained by the absorbance test of the diluted solution) at the same concentration is about 50%-65% of that of the traditional process. Combing with the anion exchange resin for decolorization and the refining with a second macroporous adsorption resin under an alkaline condition, the pesticide residues can be completely removed. By combining the aforementioned two or more clarifications through the ceramic membrane microfiltration, the problems of resin hardening and chromatography column blockage can be completely solved, the service life of the resin is extended significantly, the resin regeneration processing cycle is shortened and the production efficiency is improved.

The anion exchange resin is a basic anion exchange resin including gel-type and macroporous acrylic weak-base anion resins, acrylic acid-based strong-base and weak-base anion resins, gel-type and macroporous styrene-based strong-base anion resins, a macroporous acrylic acid strong-base anion resin, and a macroporous styrene-based weak-base anion resin, preferably D900, D941, D316, D296, D280, and is used at an amount of 70-140 kg per 1,000 kg of fresh *fructus momordicae*.

The second adsorption resin is a macroporous adsorption resin, including non-polar D101, LX-100B, LX-T28, and low-polar AB-8, and is used at an amount of 140-220 kg per 1,000 kg of fresh *fructus momordicae*; and a processing method includes after feeding, adding 1.5-3.0 BV of room-temperature purified water, then adding 0.6-1.0 BV of an aqueous solution of citric acid with a concentration of 0.3-0.6% for resin column processing, and continuously adding purified water until the pH of the resin column effluent is 5.5-7.0.

The discolored solution of *fructus momordicae* obtained through the anion exchange resin is alkaline, with a pH of about 10-11. Under this condition, it is fed into the macroporous adsorption resin column, mogroside is adsorbed, but phenolic acids, pigments, and foreign substances introduced by ion exchange resin exchange adsorption and decolorization are not adsorbed and further removed. When combined with the first macroporous adsorption resin, not only the content of mogroside can be increased, but also the pesticide residues and substances that have adverse effects on taste can be completely removed. The high-quality mogroside with good sweetness is prepared, where the content of mogroside V is 51-58 wt %. However, if the conventional method is used without a proper hot alkali treatment, the content of the obtained mogroside is relatively low, about 47-53 wt %, and the yield is also low.

In step (S2-4), the concentration is carried out under vacuum at a temperature of 50-70° C. and a vacuum degree of 0.01-0.1 MPa.

Preferably, in step (S3), the *fructus momordicae* sugar is composed of mogroside and any one of four non-sugar sweet substances (erythritol, arabinose, allulose and mannitol) or a combination thereof at any ratio. Finally, the content of mogroside V in the *fructus momordicae* sugar is 0.10-2.60%, and the sweetness is adjustable within the range of 1-10 folds of sucrose. The *fructus momordicae* sugar has a pure taste, is zero-calorie or low-calorie or has a hypoglycemic effect and a good sweetness performance, and is suitable for all populations.

Preferably, in step (S4), the *fructus momordicae* wine is composed of mogroside and a distillate during distillation. The addition amount of the mogroside is 0.05-0.30 kg of the mogroside product prepared in step (S2) per L of the distillate. The addition amount of the mogroside depends on the taste of consumers.

Preferably, in step (S4-1), the sealed fermentation is carried out for 7-30 days; the complex enzyme preparation includes the following components in parts by mass: 1.5-2.5 parts of sucrase, 1-2 parts of *rhizopus,* 2-3 parts of protease, 0.5-1 part of esterified red yeasts, 5-10 parts of *Saccharomyces cerevisiae*, and 1-2 parts of aroma-producing yeasts, and the amount of the complex enzyme preparation is 0.4-1.2 kg per 100 kg of the concentrated solution.

Preferably, the distillation temperature is 95-100° C. in step (S4-2).

The first macroporous adsorption resin effluent contains glucose, fructose, sucrose, proteins, amino acids and other substances that are not adsorbed by the resin. Through the action of microorganisms and enzymes, sucrose can be decomposed into glucose and fructose, and the glucose can produce alcohol through an anaerobic fermentation; the proteins and the amino acids can provide a nitrogen source and energy for a fermentation process; and esterified red yeasts and aroma-producing yeasts can make the fermentation system rich in various components to produce more characteristic aroma substances of *fructus momordicae*, such that the characteristic agricultural and sideline product with *fructus momordicae* characteristics, *fructus momordicae* wine, can be prepared.

Preferably, in step (S5-2), the nanofiltration for decolorization is achieved by a complete set of nanofiltration membrane equipment with a molecular weight of 300-800 Da, and collecting a permeate.

In the prior art, a retentate of a nanofiltration membrane with a certain molecular weight cut-off is collected, and then mannitol is prepared by resin chromatography and crystallization. However, the present application creatively uses pre-fermentation and small molecule cutoff nanofiltration membrane to collect the permeate only, omits the complex steps of adsorption resin chromatography in a mannitol refining process; and the mannitol can be prepared by a simple method of crystallization.

Preferably, in step (S5-3), the discolored solution is concentrated to 15-25 Brix, edible ethanol is added while hot, and the solution is naturally cooled for crystallization, and the crystallization involves adding edible ethanol, stirring same evenly, naturally cooling same at room temperature for crystallization, and filtering same to obtain a crystal I; and after the mother liquor is concentrated, recrystallizing same using the same method to obtain a crystal II, combining the crystal I and crystal II, and drying same to obtain mannitol.

*Fructus momordicae* contains a certain amount of mannitol. The physical and chemical properties of the mannitol are stable. In the present disclosure, the preparation raw material is from the first macroporous adsorption resin effluent. After the fermentation by the complex enzyme preparation, the mannitol is remained, but most pigments in the *fructus momordicae* are first adsorbed by the first macroporous adsorption resin, and unabsorbed pigments are further decomposed or removed by the fermentation and distillation of the complex preparation, and sugar and protein substances are decomposed. Therefore, through nanofiltration, only linear or small-molecule substances can pass through, while pigments, substances with a large steric hindrance, and most impurities are intercepted. The mannitol has a relatively high content in the substances passing through the nanofiltration membrane, and can be separated by crystallization using differences in concentration and solubility to prepare a high-purity mannitol product.

The present disclosure achieves the following beneficial effects.

(1) The present disclosure provides a method for freshness-preserving, storage and ripening of *fructus momordicae*. The existing storage mode of fresh *fructus momordicae* at normal temperature or in a long-term conventional cold storage is changed. ε-polylysine hydrochloride is used for inhibiting microorganisms, calcium propionate is used for mildew prevention and moisture absorption to maintain the moisture of fresh *fructus momordicae*, ozone conditioning for sterilization is combined, ethylene produced by fruit respiration is eliminated, peel pores are shrunk to reduce water loss, the metabolism of the fresh *fructus momordicae* is reduced by low temperature, and water evaporation is reduced by high humidity, that is, the synergy of the chemical agents, gas, and temperature and humidity environment achieves the long-term freshness-preserving and storage of fresh *fructus momordicae*, with a freshness-preserving period of 60-240 days. By regulating the temperature and relative humidity, and oxygen and carbon dioxide concentrations, the metabolism of the freshness-preserved *fructus momordicae* is gradually restored and improved, the damage to the fruits caused by carbon dioxide generated by respiration is reduced, and ethylene is generated, supplemented by the direct effect of exogenous ethylene and the induction of the freshness-preserved *fructus momordicae* to produce endogenous ethylene, which work together to accelerate ripening, and realize the saccharification and post-ripening of the freshness-preserved *fructus momordicae* for 15-30 days.

(2) The freshness-preserving, storage and post-ripening method of *fructus momordicae* promotes the regulation and development of the *fructus momordicae* industry. Through the long-term fresh-preservation and storage of the fresh *fructus momordicae*, the freshness-preserved *fructus momordicae* can be saccharified and post-ripened normally, so as to provide high-quality fresh *fructus momordicae* for production and processing enterprises of a *fructus momordicae* extract, baked dry *fructus momordicae*, etc., prolong a usable period of fresh *fructus momordicae*, strengthen the market control of the fresh *fructus momordicae* raw material to a certain extent, promote the healthy, stable, standardized and orderly development of the *fructus momordicae* industry, and protect the bilateral interests of farmers and enterprises.

(3) The present disclosure significantly extends the storage and post-ripening of the fresh *fructus momordicae* from 25 days in the prior art to 270 days, and reduces the bad fruit rate 22% in the prior to the bad fruit rate ≤2%, solves the problems of storage quality and saccharification and post-ripening after refrigeration of fresh *fructus momordicae*, and has progressiveness and industrial practicability.

(4) The present disclosure solves the problems of chromatography column blockage and resin hardening in the production process of *fructus momordicae*, which shortens the service life of the resin and reduces the production efficiency by means of ceramic membrane microfiltration clarification twice at high and low temperatures, macroporous adsorption resin+anion exchange resin+macroporous adsorption resin connected in series, and the treatment technology with hot water+hot alkali+purified water+dilute acid. The amount of decoloring resin is significantly reduced and the decoloring refining effect is improved, and high-quality mogroside close to pure white is obtained; and the complex steps of membrane separation, resin or extraction to remove pesticide residues are eliminated, and pesticide residues are removed completely.

(5) The present disclosure forms a core production technology system for *fructus momordicae* extraction, separation and deep processing suitable for industrial production, It includes the main and side products with clear and distinct characteristics: preparation of the leading product *fructus momordicae* extract of mogroside, preparation of the Chinese characteristic *fructus momordicae* terminal product of *fructus momordicae* sugar, which is currently the largest production and marketing product at home and abroad, fermentation of production waste liquid used to prepare mogroside to prepare the characteristic agricultural and side product of Guangxi Guilin, *fructus momordicae* wine, and then recovery and extraction of mannitol from a bottom liquor after distilling wine.

(6) The process technology of the present disclosure is advanced, simple and practical. The main process of preparing high-quality mogroside only includes water extraction, filtration and clarification, gradient processing with combined resins (the first adsorption resin+anion exchange resin+the second adsorption resin), concentration, and spray-drying, and does not involve complicated technologies such as fresh fruit drying, peeling, enzymatic hydrolysis or flocculation clarification, membrane separation, decolorization with inorganic decolorizing agents such as activated carbon and alumina, polyamide chromatography, MCI column chromatography, resin and extraction to remove pesticide residues, and improvement of sweetness of mogroside. Only through a seemingly conventional process but using an operation method that subverts existing knowledge, many problems that are encountered in the extraction, separation and deep processing of *fructus momordicae* are solved, achieving an advanced level of technology with simple and practical features.

(7) The present disclosure provides a method for industrial production and preparation of high-quality mogroside, a pharmaceutical excipient. The main process steps include first adsorption resin+anion exchange resin+second adsorption resin, and the key lies in the unconventional operation of the resin column after feeding. Among them, the first adsorption resin mainly adopts a hot alkali rapid treatment. The operation key point is that a NaOH aqueous solution at a temperature of 50-80° C., a concentration of 0.5-1.2% and a volume of 0.6-1.0 BV quickly passes through the resin column, which can significantly increase the content of mogroside and remove most pigments, thus reducing the amount of ion exchange resin and significantly improving the decolorization refining effect. The second adsorption resin is mainly to feed the basic effluent of anion exchange resin column to the chromatographic column, decolorize and refine in one step on the basis of anion exchange resin decolorization, and remove the foreign substances introduced by an exchange adsorption of the ion exchange resin that have an impact on the taste of the mogroside. The refining and decoloring effects of the mogroside are significantly improved by the treatment with the macroporous adsorption resin twice, such that the content of the mogroside is significantly increased and the color is improved. In addition, the pesticide residues are removed and the sweetness performance of the mogroside is improved, thus pharmaceutical excipient-grade high-quality mogroside with a good taste is prepared.

(8) The present disclosure provides a method for preparing mannitol. Different from the prior art, the preparation of mannitol in the present application is firstly fermenting a solution to prepare *fructus momordicae* wine, and then only performing a simple method of nanofiltration for decolorization and crystallization of a bottom liquor after distilling the wine, which eliminates the complex steps of adsorption resin chromatography. As the materials are subjected to specific refining and fermentation processes, the present application changes the previous technology of collecting a retentate of a nanofiltration membrane and adopting adsorption resin chromatography and crystallization refining, and creatively prepare the mannitol through a simple method by collecting a permeate of a nanofiltration membrane and crystallization.

BRIEF DESCRIPTION OF DRAWINGS

Detailed Description

The present disclosure is further described in conjunction with examples.

The fresh *fructus momordicae* used in the examples of the present disclosure is purchased from Yongfu County, Guilin City, Guangxi, and harvested in late October.

Unless otherwise specified, ε-polylysine hydrochloride, calcium propionate, ozone, sodium hydroxide, calcium hydroxide, and ethephon used herein are all commercially available.

Unless otherwise specified, the used purified water is self-made by a pure water machine, and the used macroporous adsorption resin, anion exchange resin, erythritol, arabinose, allulose and mannitol are all commercially available.

In the examples of the present disclosure, the content of mogroside V is determined by a high performance liquid chromatography (HPLC) described under "*fructus momordicae*" in Chinese Pharmacopoeia (2020); the content of mannitol is determined by a titration method described under "mannitol" in Chinese Pharmacopoeia (2020); the tastes of mogroside and *fructus momordicae* sugar are measured by a sensory method; and the pesticide residues in mogroside and the degree of *fructus momordicae* wine are determined by a gas chromatography (GC).

Example 1

S1 Freshness-Preserving and Post-Ripening (1) Fruit sorting and storing.

Old and green fruits and poor-quality fruits were sorted out and removed from the collected fresh *fructus momordicae*, then the intact, undamaged and mildew-free *fructus momordicae* was selected, divided into five grades according to the size: extra-large fruit, large fruit, medium fruit, small fruit, and extra-small fruit by using a special fruit measuring board for *fructus momordicae*, and separated according to the following standards: 240 small fruits, 180 medium fruits, and 140 large fruits/basket; extra-large fruits and extra-small fruits at 13.5 kilograms per basket. The fruits were packed in the baskets, stored and stacked according to the grades, with each stack of length×width×height of 5×5×5 baskets, and a stack spacing of 60 cm.

(2) Fresh-Preservation.

Fresh *fructus momordicae* stored in a warehouse were treated according to the following procedures and conditions:

Time: Stood for 220 Days.

(i) Chemical agent: a mixed aqueous solution of 0.25% ε-polylysine hydrochloride and 1.5% calcium propionate was sprayed evenly once on day 1, 27, 53, 79, 105, 130, 158, 173, and 200, respectively, with the spraying amount of 70 mL per kg of *fructus momordicae;*

(ii) Gas: an ozone cycle was activated for 45 minutes periodically every 15 days on day 1, 15, 30, 45, 60, 75, 90, 105, 120, 135, 150, 165, 180, 195, and 210, on the same day when the chemical agent was sprayed in step (i), and after each irregular inspection, with the concentration of ozone controlled at 12±3 ppm; Storage conditions: the temperature of a cold storage was set to 3° C. and the daily relative humidity to 85%, which was maintained at 60% within 12 hours after spraying the chemical agent in step (i).

(3) Post-Ripening.

The *fructus momordicae* after freshness-preserving and storage were treated according to the following procedures and conditions:

(i) Temperature: the temperature was increased by 1° C. every 4 hours, from 3° C. to 25° C.;

(ii) Relative humidity: during the heating process (0-88 hours), the relative humidity was maintained at 85%, and after the temperature reached 25° C., the relative humidity was 72%;

(iii) Air: air was changed once every 24 hours to maintain the oxygen concentration of approximately 21%; carbon dioxide was absorbed and the concentration of carbon dioxide was adjusted by a mixed solution of 0.5% NaOH and saturated $Ca(OH)_2$ with one mixed solution point set every 4 $m^2$; and (iv) Ripening: when the temperature reached 25° C., an aqueous solution of ethephon with the concentration of 600 ppm was sprayed evenly once on day 1, 5, and 10 respectively.

Time: Stood for 15 Days.

Upon inspection, the surface of more than 65% of the fresh *fructus momordicae* was turned to a yellow color like mung beans, and about 30% was turned to yellow, with the color coincidence rate≥90%; characteristic *fructus momordicae* flavor was obvious, shredded sugar appeared when touched with hands, and the taste was pure; and after 235 days of freshness-preserving (220 days) and post-ripening (15 days), the rate of bad fruits was about 1.3% (based on fresh *fructus momordicae* in storage).

In the present disclosure, the conditions for freshness-preserving and post-ripening in step 51 were further changed, while the total time for the freshness-preserving and post-ripening remained unchanged (235 days). The results were shown in Table 1 below.

TABLE 1

| Batch | Concentration of ε-polylysine hydrochloride | Concentration of calcium propionate | Spraying interval of mixed aqueous solution | Days between ozone cycles and concentration of ozone | Rate of bad fruits |
|---|---|---|---|---|---|
| 1 | 0.25% | 1.5% | 26 days | 15 days, 12 ± 3 ppm | 1.3% |
| 2 | 0.1% | 2.0% | 26 days | 15 days, 12 ± 3 ppm | 1.4% |
| 3 | 0.3% | 1.0% | 26 days | 15 days, 12 ± 3 ppm | 1.6% |
| 4 | 0.25% | 1.5% | 20 days | 15 days, 12 ± 3 ppm | 1.3% |
| 5 | 0.25% | 1.5% | 30 days | 15 days, 12 ± 3 ppm | 1.5% |
| 6 | 0.1% | 2.0% | 26 days | None | 2.1% |
| 7 | None | 1.5% | 26 days | 15 days, 12 ± 3 ppm | 2.2% |
| 8 | 0.3% | None | 26 days | 15 days, 12 ± 3 ppm | 2.4% |

The storage conditions in step (2) during freshness-preserving were changed as follows: the temperature of the cold storage was set to 3° C. and the daily relative humidity to 85 RH %, which was maintained at 60 RH % within 12 hours after spraying the chemical agent in step (i). After testing, there was no obvious change in the freshness-preserving time; but the rate of bad fruits increased from 1.3% to 1.7%.

Therefore, in summary, the mixed solution sprayed during the freshness-preserving process of the present disclosure contained 0.25% ε-polylysine hydrochloride and 1.5% calcium propionate, with a spraying interval of 26 days; and the ozone cycle was activated every 15 days to maintain the ozone concentration in the warehouse at a level of 12±3 ppm.

S2, Preparation of Mogroside:

(1) Water extraction. 1,500 kg of fresh *fructus momordicae* were taken after saccharification and post-ripening with the average content of mogroside V at 0.49 wt %. The *fructus momordicae* was crushed with seeds intact by using a *fructus momordicae* crusher, and the crushed materials were transported to a 6 $m^3$ extraction tank with tap water.

Operating conditions: temperature: 92° C.; time: 2.0, 1.5, and 0.5 hours; frequency: 3 times; water addition amount: 4,000 L, 3,000 L, and 4,000 L; stirring method: compressed air backflushing was started for 5 minutes every 15 minutes. After each extraction, an extract was filtered, the residues from the first and second extractions were extracted for the third time, a third extract was collected separately, and the first and second extracts were combined to obtain 6,200 L of an extract.

(2) Filtration and clarification. The temperature of the extract was reduced to 55° C. through a plate heat exchanger, firstly, the extract was subjected to horizontal spiral sedimentation and centrifugation, followed by disc centrifugation, and then subjected to microfiltration using a first complete set of ceramic membrane equipment with the material of zirconia and a pore size of 500 nm, and a filtrate was collected. The filtrate was continuously cooled to 24° C. through the plate heat exchanger, and then subjected to microfiltration using a second complete set of ceramic membrane equipment with the material of zirconia and a pore size of 200 nm, and a filtrate was collected to obtain a ceramic membrane clear solution.

(3) Gradient processing with combined resins.

A first macroporous adsorption resin. 700 kg of D101 macroporous adsorption resin was pre-installed into a stainless steel chromatography column, and the resin column was subjected to acid-base regeneration for later use. The ceramic membrane clear solution was fed into the macroporous adsorption resin column, after feeding, 1,600 L of hot purified water at a temperature of 70° C. was added, a feed effluent and 1,200 L of a purified water-washing solution were collected to obtain an effluent. Then a NaOH aqueous solution at a temperature of 55° C., a concentration of 0.8%, and a volume of 550 L at a flow rate of 1,400 L/h was used for resin column processing. Then room-temperature purified water was added at a flow rate of 850 L/h until the pH of the resin column effluent was 7.0. Then desorption was performed with 1,800 L of 65% edible ethanol and a desorbed solution was collected. The desorbed solution was concentrated under a reduced pressure at a vacuum of −0.09 MPa and a temperature of 62° C., and ethanol was recovered until there is no alcohol odor to obtain an adsorption resin processed solution.

Anion exchange resin. 110 kg of D941 weakly basic anion exchange resin was pre-installed into a stainless steel chromatography column internally lined with plastic, and subjected to acid-base regeneration for later use. The sugar degree of an adsorption resin-processed solution was adjusted to 6 Brix, the solution was feed into the basic anion exchange resin column, and after feeding, 500 L of purified water was added to wash the resin column, and a feed effluent and a water-washing solution were collected in sequence.

A second macroporous adsorption resin. 240 kg of white D101 macroporous adsorption resin with pigments not adsorbed was pre-installed in a stainless steel chromatography column and treated with 90% ethanol and purified water for later use. The anion exchange resin column feed effluent and the water-washing solution were fed into the macroporous adsorption resin column in sequence. After feeding, 500 L of room-temperature purified water was added, 200 L of an aqueous solution of citric acid with the concentration of 0.4% was added for resin column processing, then 600 L of purified water was continuously added until the pH of the resin column effluent was 6.3, then desorption was performed with 520 L of 65% edible ethanol, and a desorbed solution was collected to obtain a combined resin refined solution.

(4) Concentration. The combined resin refined solution was concentrated under a reduced pressure to 18 Baume degrees at a vacuum of −0.09 MPa and a temperature of 63° C. to obtain a vacuum-concentrated solution.

(5) Spray-drying. An air inlet temperature of spray-drying was adjusted to 185° C. and an air outlet temperature to 87° C., and the vacuum-concentrated solution was dried to obtain 11.4 kg of mogroside. After testing, the content of mogroside V was 57.11 wt %, the yield of the mogroside V was 88.56%, and a white powder was obtained.

S3. Preparation of *Fructus Momordicae* Sugar:

(1) 0.48 kg of the mogroside from step (2) was taken and dissolved with 8 kg of purified water as an adhesive, where the solid content was 5.66%.

(2) 99.52 kg of erythritol was fed into a fluidized bed at a temperature of 72° C. and a vacuum degree of −0.088 MPa, the adhesive was sprayed evenly at a speed of 3 kg/h, the materials were dried to obtain 99.1 kg of original *fructus momordicae* sugar. The sweetness of the obtained *fructus momordicae* sugar was about twice that of sucrose.

S4. Preparation of *Fructus Momordicae* Wine:

(1) Liquid fermentation of first adsorption resin effluent. The first adsorption resin feed effluent in step (2) and 1,200 L of a purified water-washing solution were collected, and concentrated to 13 Brix to obtain 825 kg of a concentrated solution. The solution was cooled to room temperature, the ambient temperature was adjusted to 25° C., 5.0 kg of a complex preparation (specific composition: 1.8 parts of sucrase, 1.2 parts of *rhizopus,* 2.5 parts of protease, 0.6 parts of esterified red yeasts, 9 parts of *Saccharomyces cerevisiae*, and 1.4 parts of aroma-producing yeasts) was added, and the materials were stirred evenly and subjected to a sealed fermentation for 20 days until a wine aroma was mellow to obtain a fermentation liquor.

(2) Distillation. The fermentation liquor was distilled and rectified, a distillation bottom liquor and a distillate were respectively collected, and the distillate was *fructus momordicae* base wine, which had the alcohol content of 53% vol and was 25.3 kg.

(3) Blending of mogroside. 10 L of the 53% vol distilled *fructus momordicae* base wine was taken, 0.005 kg of the mogroside in step (2) was added, and the materials were mixed evenly and canned to obtain a *fructus momordicae* wine.

S5. Preparation of Mannitol:

(1) Microfiltration of distillation bottom liquor. The distillation bottom liquor was microfiltrated through a complete set of ceramic membrane equipment with the material of zirconia and a pore size of 500 nm, and a filtrate was collected to obtain a ceramic membrane clear solution.

(2) Nanofiltration for decolorization. The ceramic membrane clear solution was decolorized through a complete set of nanofiltration membrane equipment with a molecular weight cut-off of 500 Da, and a filtrate was collected to obtain a discolored solution.

(3) Crystallization. The discolored solution was concentrated under a reduced pressure to 22 Brix to obtain 115.2 kg of a concentrated solution. 150 L of 95% edible ethanol was added while hot, the materials were stirred evenly, naturally cool at room temperature to crystallize, and filtered to obtain a crystal I; and a mother liquor was concentrated and recrystallized once using the same method to obtain a crystal II.

The crystals I and II were combined and dried to obtain 4.3 kg of mannitol.

After testing, the content of mogroside V in the mogroside was 57.11%, the mogroside was off-white powder, no pesticide residue was detected, and the taste was pure. The sweetness of *fructus momordicae* sugar was twice that of sucrose and lasted for 6.5 seconds. The alcohol content of the *fructus momordicae* wine was 53% vol. The content of the mannitol was 99.20%.

Example 2

Other conditions and operations were the same as those in Example 1, but the difference was that the preparation process of mogroside in step S2 was as follows:

Steps (1) and (2) are the same as those in Example 1.

(3) Gradient processing with combined resins.

The first macroporous adsorption resin. 825 kg of LX-100B macroporous adsorption resin was pre-installed into a stainless steel chromatography column and subjected to acid-base regeneration for later use. A ceramic membrane clear solution was fed into the macroporous adsorption resin column, and after feeding, 1,500 L of hot purified water at a temperature of 80° C. was added, and a feed effluent and 1,200 L of a purified water-washing solution was collected to obtain an effluent. Then a NaOH aqueous solution at a temperature of 50° C., a concentration of 0.9%, and a volume of 800 L was added at a flow rate of 1,500 L/h for resin column processing. Then room-temperature purified water was added at a flow rate of 800 L/h until the pH of the resin column effluent was 7.0. Then desorption was performed with 2,000 L of 60% edible ethanol and a desorbed solution was collected. The desorbed solution was concentrated under a reduced pressure at a vacuum of −0.09 MPa and a temperature of 62° C. and ethanol was recovered until there was no alcohol odor to obtain an adsorption resin-processed solution.

Anion exchange resin. 120 kg of D900 weakly basic anion exchange resin was pre-installed into a stainless steel chromatography column internally lined with plastic and subjected to acid-base regeneration for later use. The sugar degree of a adsorption resin-processed solution was adjusted to 6 Brix, the solution was feed into the basic anion exchange resin column, and after feeding, 500 L of purified water was added to wash the resin column. A feed effluent and a water-washing solution were collected in sequence.

A second macroporous adsorption resin. 280 kg of LX-100B macroporous adsorption resin was pre-installed in a stainless steel chromatography column and treated with 90% ethanol and purified water for use. The anion exchange resin column feed effluent and the water washing solution were fed into the macroporous adsorption resin column in sequence. After feeding, 600 L of room-temperature purified water was added, 200 L of an aqueous solution of citric acid with the concentration of 0.4% was added for resin column processing, and then 800 L of purified water was added until the pH of the resin column effluent was 6.4. Then desorption was performed with 550 L of 65% edible ethanol and a desorbed solution was collected to obtain a combined resin refined solution.

(4) Concentration. The combined resin refined solution was concentrated to 18 Baume degrees at a vacuum of −0.09 MPa and a temperature of 63° C. to obtain a vacuum-concentrated solution.

(5) Spray-drying. An air inlet temperature of spray-drying was adjusted to 185° C. and an air outlet temperature was 87° C., and the vacuum-concentrated solution was dried to obtain 11.4 kg of mogroside. After testing, the content of mogroside V was 56.68 wt %, the yield of mogroside V was 87.91%, and a white powder was obtained.

Example 3

Other conditions and operations were the same as those in Example 1, but the difference was the preparation of *fructus momordicae* sugar in S3:

(1) 0.48 kg of mogroside was taken from step (2) and dissolved with 8 kg of purified water as an adhesive, where the solid content was 5.66%.

(2) 50.0 kg of erythritol and 49.0 kg of allulose were fed into a fluidized bed at a temperature of 72° C. and a vacuum degree of −0.088 MPa, the adhesive was sprayed evenly at a speed of 3 kg/h and dried to obtain 98.5 kg of original *fructus momordicae* sugar. The sweetness of the obtained *fructus momordicae* sugar is about twice that of sucrose.

Example 4

Other conditions and operations were the same as those in Example 1, but the difference was the preparation of *fructus momordicae* wine in S4:

(1) Liquid fermentation of first adsorption resin effluent. The first adsorption resin feed effluent in step (2) and 1,200 L of a purified water-washing solution were collected, and concentrated to 20 Brix to obtain 550 kg of a concentrated solution. The concentrated solution was cooled to room temperature, the ambient temperature was adjusted to 25° C., 4.5 kg of a complex preparation (specific composition: 1.8 parts of sucrase, 1.2 parts of *rhizopus,* 2.5 parts of protease, 0.6 parts of esterified red yeasts, 9 parts of *Saccharomyces cerevisiae*, and 1.4 parts of aroma-producing yeasts) was added, and the materials were stirred evenly and subjected to a sealed fermentation for 30 days until the wine aroma was mellow obtain a fermentation liquor.

(2) Distillation. The fermentation liquor was distilled and rectified, a distillation bottom liquor and a distillate were collected, and the distillate was *fructus momordicae* base wine, which had the alcohol content of 26% vol and was 51.2 kg.

(3) Blending of mogroside. 10 L of 26% vol of the distilled *fructus momordicae* base wine was taken, 0.030 kg of the mogroside in step (2) was added, and the materials were mixed evenly and canned to obtain a *fructus momordicae* wine.

Example 5

Other conditions and operations were the same as those in Example 1, but the difference was that in the filtration for clarification of step S2(2), the temperature of the twice microfiltration through a complete set of ceramic membrane equipment was 55° C. After the obtained clear solution was fed to the chromatography column, due to the presence of some viscous substances, the resin column was hardened to a certain extent, thereby reducing the adsorption of mogroside by the macroporous adsorption resin. The content of mogroside V was 56.24% and the yield was 85.63%.

Comparative Example 1

Other conditions and operations were the same as in Example 1, except that in the gradient processing with combined resins in step S2(3), the first macroporous adsorption resin was not treated with a hot alkaline solution, but treated conventionally: the ceramic membrane clear solution was fed into the macroporous adsorption resin column, after feeding, room-temperature purified water was added until an effluent was clear, transparent and almost colorless (the water amount was relatively large), then desorption was performed with 65% edible ethanol, a desorbed solution was concentrated under a reduced pressure at a vacuum of −0.09 MPa and a temperature of 62° C., and ethanol was recovered until there was no alcohol odor to obtain an adsorption resin-processed solution. The subsequent steps were the same as those in Example 1. The solution was fed into the anion exchange resin column and the second macroporous adsorption resin column in sequence.

The content of mogroside V in mogroside in the final product was 51.35% and the yield was 83.51%. There was no significant effect on other products.

Comparative Example 2

Other conditions and operations were the same as those in Example 1, except that in the gradient processing with combined resins in step S2(3), the processing with the anion exchange resin was omitted. The final mogroside was a light yellow powder. The content of mogroside V was 42.63%, and the yield of mogroside was 88.25%. It indicates that the anion exchange resin was the key to achieve the content of mogroside V in mogroside to be more than 50%. In addition, the taste of the mogroside product obtained without the anion exchange resin operation was not as good as that in Example 1, and was astringent.

The invention claimed is:

1. A method for producing mogroside, *fructus momordicae* sugar/wine and mannitol from fresh *fructus momordicae*, comprising the following steps:

S1, freshness-preserving and post-ripening, which comprises:

S11: sorting out fresh *fructus momordicae* from a harvest, and storing the sorted fresh *fructus momordicae* in a warehouse;

S12: standing the fresh *fructus momordicae* in the warehouse for 60-240 days at a temperature of 2-6° C. and a relative humidity of 80-90%, intervally spraying a mixed aqueous solution comprising ε-polylysine hydrochloride and calcium propionate, while-intervally activating ozone cycles, with the proviso that the relative humidity within 12 hours after each spraying of the mixed aqueous solution is 55-65%; and S13: raising the temperature to 22-26° C. at a heating rate of 0.15-0.35° C./h in the warehouse, maintaining the relative humidity of 80-90% during the heating process, and a relative humidity of 70-80% after reaching the target temperature, changing air every 22-26 hours to maintain a normal oxygen concentration, absorbing carbon dioxide to adjust the concentration of carbon dioxide with an alkaline solution, and spraying an aqueous solution of ethephon every 4-6 days, wherein a duration of S13 is 15-30 days;

S2, preparation of mogroside, which comprises:

S21: crushing the *fructus momordicae* obtained from S13 and extracting the crushed *fructus momordicae* with water to obtain an extract;

S22: subjecting the extract to microfiltration using ceramic membrane to obtain a clear solution;

S23: subjecting the clear solution to adsorption and desorption in a first macroporous adsorption resin column, an anion exchange resin column, and a second macroporous adsorption resin column sequentially; and combining desorption effluents to obtain a refined solution;

S24: concentrating the refined solution to a concentration of 17-25 Baume degree to obtain a concentrated solution; and S25: spray-drying the concentrated solution to obtain mogroside;

S3, preparation of *fructus momordicae* sugar, comprising:

S31: dissolving an amount of the mogroside obtained from step S2 in purified water to obtain an adhesive; and S32: feeding a sweetener and spraying the adhesive into a boiling granulator for boiling granulation, and drying the resulting granulates to obtain the *fructus momordicae* sugar, wherein the sweetener is selected from erythritol, arabinose, allulose, mannitol, and mixtures thereof;

S4, preparation of *fructus momordicae* wine, comprising:

S41: collecting an adsorption effluent from the first macroporous adsorption resin column, combining the adsorption effluent with a water-washing solution obtained from rinsing the first macroporous adsorption resin column to obtain a mixed effluent, concentrating the mixed effluent to 5-25 Brix, and fermenting the concentrated mixed effluent in the presence of an enzyme preparation to obtain a fermentation liquor;

S42: distilling the fermentation liquor, collecting a distillation bottom liquor and a distillate; and S43: adding the mogroside obtained in step S2 to the distillate to obtain the *fructus momordicae* wine; and S5: preparation of mannitol, which comprises:

S51: filtering the distillation bottom liquor obtained from S42 to obtain a filtrate;

S52: subjecting the filtrate from S51 to nanofiltration for decolorization to obtain a discolored solution; and S53: concentrating the discolored solution and adding ethanol to form a mixture, and cooling the mixture for crystallization to obtain mannitol.

2. The method of claim 1, wherein the mixed aqueous solution in S12 has a concentration of ε-polylysine hydrochloride of 0.1-0.3%, and a concentration of calcium propionate of 1.0-2.0%, and the mixed aqueous solution is sprayed evenly once every 25-30 days at an amount of 50-100 mL of the mixed aqueous solution per kg of *fructus momordicae*; and/or each ozone cycle is carried out 40-60 minutes at an amount of ozone of 5-15 ppm every 14-16 days or after a warehouse door is opened and closed.

3. The method of claim 1, wherein in S13, the alkaline solution is a mixed solution of NaOH and Ca (OH) 2, wherein the concentration of NaOH is 0.2-1.0 wt % and the Ca (OH) 2 is saturated lime water; and/or the concentration of ethephon in the aqueous solution of ethephon is 400-800 ppm, and 40-80 mL of the aqueous solution of ethephon is sprayed to per kg of *fructus momordicae*.

4. The method of claim 1, wherein in S22, the microfiltration is performed two to four times, and the temperature is reduced from 45-60° C. to 15-30° C. during the microfiltration.

5. The method of claim 1, wherein S23 specifically comprises:

1) running the clear solution through the first macroporous adsorption resin column, followed by running water and then running an alkaline solution at 50-80° C. through the first macroporous adsorption resin column, then rinsing the first macroporous adsorption resin column with water at room temperature until the effluent has a pH of 6.8-7.5, then carrying out desorption in the first macroporous adsorption resin column with hydrous ethanol, collecting a first desorption effluent, and concentrating and recovering ethanol from the first desorption effluent to obtain an adsorption resin-processed solution;

2) adjusting a sugar content of the adsorption resin-processed solution to 4-8 Brix, and running the resulting adsorption resin-processed solution through the anion exchange resin column, and running 3-5 bed volume (BV) purified water to rinse the anion exchange resin column after, and collecting the effluent and the water-washing solution; and 3) sequentially running the anion exchange resin column effluent, the water-washing solution, and purified water through the second macroporous adsorption resin column, running purified water through the second macroporous adsorption resin column, followed by running an aqueous solution of citric acid through the second macroporous adsorption resin column, and then running purified water until a pH of the resin column effluent is 5.5-7.0, then desorbing with hydrous ethanol, and collecting a second desorption effluent to obtain the refined solution.

6. The method of claim 5, wherein the first adsorption resin column contains a macroporous adsorption resin selected from non-polar D101, LX-100B, LX-T28, and low-polar AB-8, and is used at an amount of 400-550 kg per 1,000 kg of fresh *fructus momordicae*; and/or the anion exchange resin column contains a basic anion exchange resin selected from gel-type and macroporous acrylic weak-base anion resins, acrylic acid-based strong-base and weak-base anion resins, gel-type and macroporous styrene-based strong-base anion resins, a macroporous acrylic acid strong-base anion resin, and a macroporous styrene-based weak-base anion resin, and is used at an amount of 70-140 kg per 1,000 kg of fresh *fructus momordicae*; and/or the second adsorption resin column contains a macroporous adsorption resin; selected from non-polar D101, LX-100B, LX-T28, and low-polar AB-8, and is used at an amount of 140-220 kg per 1,000 kg of fresh *fructus momordicae*.

7. The method of claim 1, wherein in step S3, the content of mogroside in the *fructus momordicae* sugar is 0.10-2.60%, and/or in step S4, the content of mogroside in the *fructus momordicae* wine is 0.01-0.04% (w/v).

8. The method of claim 1, wherein in S41, fermenting the concentrated mixed effluent is carried out in a sealed container for 7-30 days; the enzyme preparation comprises the following components in parts by mass: 1.5-2.5 parts of sucrase, 1-2 parts of *rhizopus*, 2-3 parts of protease, 0.5-1 part of esterified red yeasts, 5-10 parts of *saccharomyces cerevisiae*, and 1-2 parts of aroma producing yeasts, and the enzyme preparation is used at an amount of 0.4-1.2 kg per 100 kg of the concentrated mixed effluent.

9. The method of claim 1, wherein in S52, the nanofiltration for decolorization has a molecular weight cut-off of 300-800 Da, and in S53, the discolored solution is concentrated to 15-25 Brix, edible ethanol is added therein, followed by naturally cooling for a first crystallization concentrating the remaining liquid from the first crystallization, and then recrystallizing the concentrated liquid to obain a crystal II, and combining and drying the crystal I and the crystal II to obtain mannitol.

* * * * *